United States Patent
Yelton et al.

(10) Patent No.: US 8,635,088 B2
(45) Date of Patent: Jan. 21, 2014

(54) MEDICAL FACILITY BED AVAILABILITY

(75) Inventors: Paul A. Yelton, Cold Spring, KY (US); Frederick C. Ryckman, West Chester, OH (US)

(73) Assignee: Cincinnati Children's Hospital Medical Center, Cincinnati, OH (US)

( * ) Notice: Subject to any disclaimer, the term of this patent is extended or adjusted under 35 U.S.C. 154(b) by 21 days.

(21) Appl. No.: 12/903,288

(22) Filed: Oct. 13, 2010

(65) Prior Publication Data

US 2011/0087502 A1 Apr. 14, 2011

Related U.S. Application Data

(60) Provisional application No. 61/251,578, filed on Oct. 14, 2009.

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ............................................................ 705/3
See application file for complete search history.

(56) References Cited

U.S. PATENT DOCUMENTS

| 4,135,241 | A  | * | 1/1979  | Stanis et al. | 705/28 |
|-----------|----|---|---------|--------------|--------|
| 5,991,728 | A  | * | 11/1999 | DeBusk et al. | 705/2 |
| 7,315,535 | B2 |   | 1/2008  | Schuman | |
| 7,539,623 | B1 | * | 5/2009  | Wyatt | 705/5 |
| 7,716,066 | B2 | * | 5/2010  | Rosow et al. | 705/2 |
| 7,720,695 | B2 | * | 5/2010  | Rosow et al. | 705/2 |
| 7,734,479 | B2 | * | 6/2010  | Rosow et al. | 705/2 |
| 7,756,723 | B2 | * | 7/2010  | Rosow et al. | 705/2 |
| 7,774,215 | B2 | * | 8/2010  | Rosow et al. | 705/2 |
| 7,912,736 | B2 | * | 3/2011  | Wyatt | 705/3 |
| 8,010,386 | B2 | * | 8/2011  | Wyatt | 705/4 |
| 2003/0074222 | A1 | * | 4/2003  | Rosow et al. | 705/2 |
| 2004/0128168 | A1 | * | 7/2004  | Wyatt | 705/2 |
| 2004/0243446 | A1 | * | 12/2004 | Wyatt | 705/2 |
| 2006/0004605 | A1 |   | 1/2006  | Donoghue et al. | |
| 2006/0143045 | A1 |   | 6/2006  | Nacey | |
| 2007/0239484 | A1 | * | 10/2007 | Arond et al. | 705/2 |
| 2008/0027754 | A1 |   | 1/2008  | Auker et al. | |
| 2008/0065434 | A1 | * | 3/2008  | Rosow et al. | 705/5 |
| 2010/0228565 | A1 | * | 9/2010  | Rosow et al. | 705/2 |

* cited by examiner

*Primary Examiner* — Michael Fuelling
(74) *Attorney, Agent, or Firm* — Baker & Hostetler LLP

(57) ABSTRACT

Methods, systems, devices and/or apparatus related to predicting availability of medical facility beds. Specifically, the disclosed methods, systems, devices and/or apparatus relate to determining which beds in the medical facility are available or unavailable at specific time periods (including past, present and/or future time periods).

16 Claims, 11 Drawing Sheets

| DAILY DISCHARGE PREDICTION WORKSHEET Current Date: 9/2/09 | | | | Potential Discharge? | | Check if Completed Dash if not | | | | | | Check Predicted Discharge Time | | | | Predicted Discharge Date |
|---|---|---|---|---|---|---|---|---|---|---|---|---|---|---|---|---|
| ROOM # | PATIENT LAST NAME | PATIENT MRN | SERVICE | High Reliability | Contingent | 1-Order Complete? | 2-Summary Complete? | 3-Prescripts Written? | 4-DME Ordered? | 5-Social Issues Identified? | 6-Transport Ready? | 8 AM -11 AM | 11 AM – 2 PM | 2 PM – 5 PM | 5 PM – 8 AM | |
| E1 | WILLIAMS | 4234098 | BLUE | | | | | | | | | X | | | | 9/2/09 |
| E2 | | | | | | | | | | | | | | | | |
| E3 | OSCAR | 8274027 | RED | | | | | | | | | X | | | | 9/2/09 |
| E4 | JONES | 6302763 | RED | | | | | | | | | | X | | | 9/2/09 |
| E5 | PENNY | 4322113 | GREEN | | | | | | | | | | | | X | 9/2/09 |
| E6 | FRANKS | 7654456 | GREEN | | | | | | | | | | | X | | 9/2/09 |
| E7 | TALBOT | 2412343 | BLUE | | | | | | | | | | | | | 9/8/09 |
| E8 | KENNEDY | 4352652 | RED | | | | | | | | | | | | | 9/14/09 |
| E9 | JOHNSON | 6584538 | RED | | | | | | | | | | | | | 9/23/09 |

MEDICAL FACILITY BED AVAILABILITY

CROSS-REFERENCE TO RELATED APPLICATIONS

This Application claims priority from U.S. Provisional Application, Ser. No. 61/251,578, filed Oct. 14, 2009; the disclosure of which is incorporated herein by reference.

BACKGROUND

Medical facilities such as hospitals, doctor's offices, urgent care facilities and inpatient/outpatient facilities may desire to operate as efficiently as possible. Efficient operations may directly correspond to increased patient flow, increased productivity, increased profits, improved demand/capacity matching, and more satisfied patients, guests, employees, practitioners and administrators. To facilitate efficient operations, medical facilities may desire to determine and/or view patients projected to need a bed. Additionally, medical facilities may desire to determine what patients may be using which beds at any given time (i.e., past, present and/or future times).

Therefore, medical facilities may desire a solution to enhance operating efficiencies and, ultimately, provide better service to their guests, employees, practitioners and administrators.

SUMMARY

Methods, systems, devices and/or apparatus related to predicting availability of medical facility beds are disclosed. Specifically, the disclosed methods, systems, devices and/or apparatus relate to determining which beds in the medical facility are available or unavailable at specific time periods (including past, present and/or future time periods).

A first aspect of the disclosure may provide a system for predicting availability of a plurality of medical facility beds for use by a plurality of medical facility patients. The system is in communication with at least one medical facility patient database configured to store patient data related to biographical information, medical information and/or location information for the plurality of medical facility patients. The system may include: at least one medical facility bed database configured to store medical facility bed data related to location information and/or availability information for the plurality of medical facility beds; a medical facility patient stay component configured to receive a predicted length of stay data for at least one medical facility patient of the plurality of medical facility patients; a medical facility bed availability component configured to reserve at least one medical facility bed of the plurality of medical facility beds for the at least one medical facility patient of the plurality of medical facility patients based, at least in part, on the predicted length of stay data for the respective at least one medical facility patient; and a medical facility bed reporting component configured to output medical facility bed availability information in a table configuration based, at least in part, on the reservations of the medical facility bed availability component. The table configuration may represent an availability of each of the plurality of medical facility beds. The table configuration may include a plurality of rows and a plurality of columns, where each of the plurality of rows represents one of a respective medical facility bed or a respective date, and each of the plurality of columns represents the other one of a respective medical facility bed or a respective date.

In a more detailed embodiment of the first aspect, the medical facility reporting component may be configured to generate a graphical representation of the medical facility bed availability information. In a further detailed embodiment, the graphical representation may be transmitted to a display device and/or a printing device.

In an alternate detailed embodiment of the first aspect, the medical facility bed reporting component may be further configured to display a visual representation of the availability of the plurality of medical facility beds during a past time period, a present time period and/or a future time period.

In another alternate detailed embodiment of the first aspect, the medical facility reporting component may be further configured to generate a report depicting the medical facility bed availability information.

In another alternate detailed embodiment of the first aspect, the medical facility bed availability information may include a plurality of attributes, where the plurality of attributes relate to the predicted length of stay data. In a further detailed embodiment, each of the plurality of may be represented by a respective color. Alternatively, the plurality of attributes may include a predicted length of stay data is present attribute, a predicted length of stay data is not present attribute, an end of the predicted length of stay is approaching attribute, an end of the predicted length of stay has occurred attribute, and/or a medical facility patient has been discharged prior to the end of the predicted length of stay attribute. In a further detailed embodiment, the predicted length of stay data is present attribute is represented by a first color, the predicted length of stay data is not present attribute is represented by a second color, an end of the predicted length of stay is approaching attribute is represented by a third color, an end of the predicted length of stay has occurred attribute is represented by a fourth color, and the medical facility patient has been discharged prior to the end of the predicted length of stay attribute is represented by a fifth color.

In another alternate detailed embodiment of the first aspect, the system may further include a stay prediction component configured to estimate the predicted length of stay data based, at least in part, on historical length of stay data for at least one of the plurality of medical facility patients.

In another alternate detailed embodiment of the first aspect, the system may further include an input component configured to receive predicted length of stay data for the at least one medical facility patient from at least one medical practitioner. In a further detailed embodiment, the input component may be configured to receive diagnosis data.

In another alternate detailed embodiment of the first aspect, the system may further include a patient discharge component configured to generate a list of discharge tasks to be completed by at least one medical practitioner prior to discharging the at least one of the medical facility patients.

In another alternate detailed embodiment of the first aspect, the medical information may include treatment information related to a disease, an ailment, a diagnosis, a symptom, a complaint, an administered treatment and/or a proposed treatment.

In another alternate detailed embodiment of the first aspect, the system may further include an inventory prediction component configured to monitor an amount of stocked medical supplies related to a treatment of each respective one of the plurality of medical facility patients, and further configured to estimate an amount of predicted medical supplies needed to perform the treatment of each respective one of the plurality of medical facility patients. In a further detailed embodiment, the inventory prediction component may be further configured to generate a report depicting at least one of the amount of stocked medical supplies and the amount of predicted medical supplies. In yet a further detailed embodiment, the inventory prediction component may be further configured to interface with a third party medical supplies supplier to order additional medical supplies.

In another alternate detailed embodiment of the first aspect, the system may further include an artificial intelligence component configured to generate the predicted length of stay data based, at least in part, on a knowledge base that associates historical patient stay data with other historical data. In a more detailed embodiment, the other historical data may include patient medical history, patient insurance data, historical disease/ailment data, historical treatment data, historical length of stay data and/or historical recovery time data.

A second aspect of the present disclosure may provide one or more non-transitory computer memory devices including computer readable instructions for controlling a computerized system to perform a method of predicting availability of a plurality of medical facility beds, where the instructions may include the steps of: receiving data related to a predicted length of stay of at least one of a plurality of medical facility patients; allocating at least one non-allocated medical facility bed to each of the plurality of medical facility patients based, at least in part, on the received data; and generating a report based, at least in part, on the allocating of the non-allocated medical facility beds, where the report includes a table having a plurality of rows and a plurality of columns, where each of the plurality of rows represents a respective medical facility bed and each of the plurality of columns represents a respective date, and where the table represents an availability of each of the plurality of medical facility beds. A third aspect of the present disclosure may provide one or more Web servers including such non-transitory memory devices.

A fourth aspect of the present disclosure may provide one or more non-transitory computer memory devices including computer readable instructions for controlling a computerized system to perform a method of predicting availability of a plurality of medical facility beds, where the instructions may include the steps of: receiving predicted length of stay data related to a first patient and a second patient; storing the predicted length of stay data in at least one patient database; reserving, for a first future time period, a first bed for a first patient, provided the first bed has not been previously reserved during at least a portion of the first future time period, the first future time period being associated with the predicted length of stay data related to the first patient; reserving, for a second future time period, a second bed for a second patient, provided the second bed has not been previously reserved during at least a portion of the second future time period, the second future time period being associated with the predicted length of stay data related to the second patient; and generating a report based, at least in part, on the reserving of the first bed and the reserving of the second bed, where the report includes a table having at least two rows and a plurality of columns, where each of the plurality of columns represents a respective date, where a first row of the at least two rows represents the first bed and a second row of the at least two rows represents the second bed, and where the table represents an availability of each of the first bed and the second bed. In a more detailed aspect the computer readable instructions may further include the steps of generating predicted length of stay data related to a first patient and/or a second patient based, at least in part, on a knowledge base that associates historical patient stay data related the first patient and/or the second patient with other historical data. In yet a more detailed aspect, the other historical data may include patient medical history, patient insurance data, historical disease/ailment data, historical treatment data, historical length of stay data and/or historical recovery time data.

BRIEF DESCRIPTION OF THE DRAWINGS

The foregoing and other features of the present disclosure will become more fully apparent from the following description and appended potential points of novelty, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 6 is a diagram depicting an interface of another example embodiment of the present invention.

FIG. 7 is a diagram depicting an interface of yet another example embodiment of the present invention.

FIG. 8 depicts an example report that may be generated by an example embodiment of the present invention.

DETAILED DESCRIPTION

Figure 1:
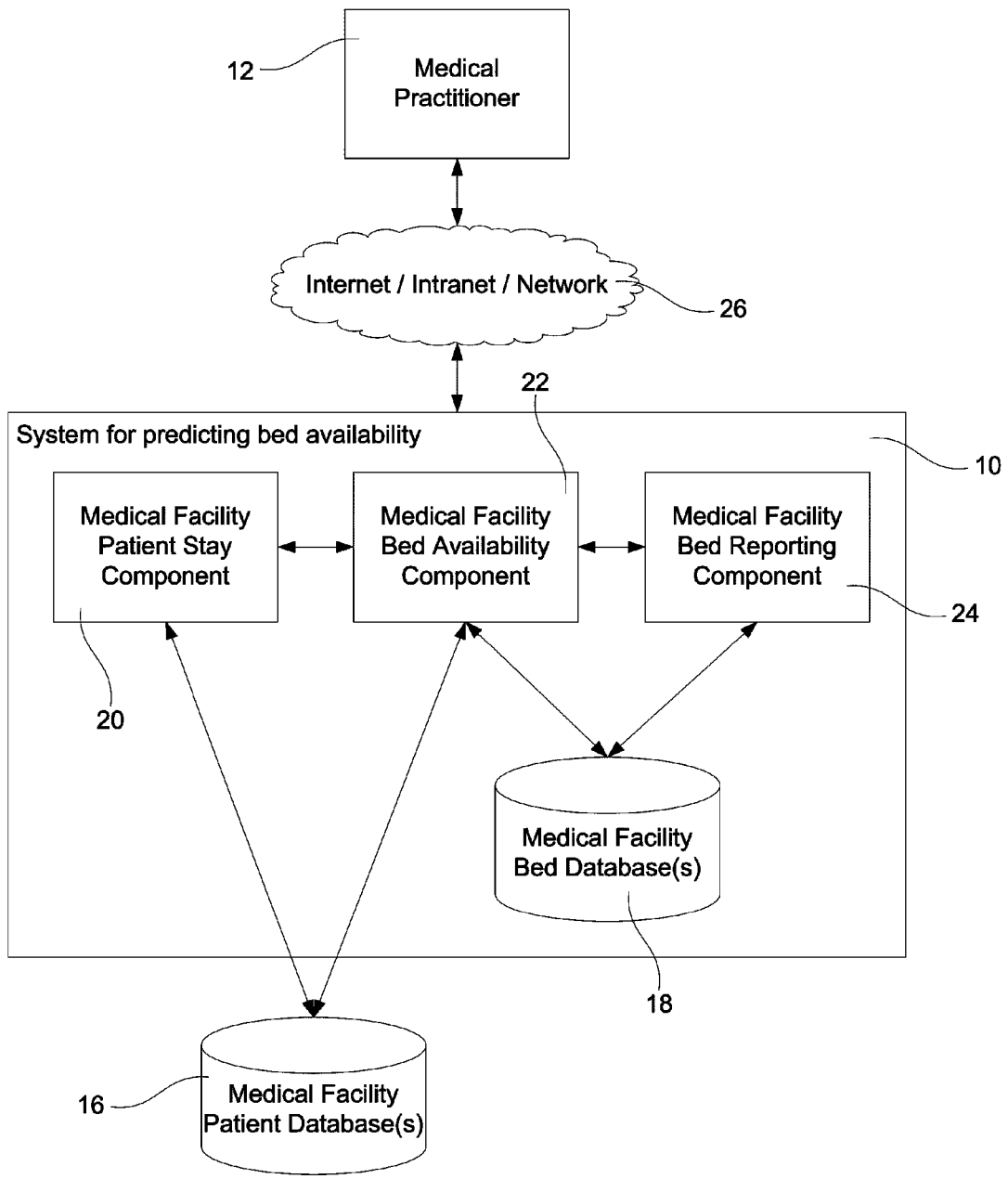
FIG. 1 is a diagram depicting an example embodiment of the present invention.

In the following detailed description, reference is made to the accompanying drawings, which form a part hereof. In the drawings, similar symbols typically identify similar components, unless context dictates otherwise. The illustrative embodiments described in the detailed description, and drawings to be limiting to those precise embodiments. Other embodiments may be utilized, and other changes may be made, without departing from the spirit or scope of the subject matter presented and claimed here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

This disclosure is drawn to methods, systems, devices and/or apparatus related to predicting availability of medical facility beds. Specifically, the disclosed methods, systems, devices and/or apparatus relate to determining which beds in the medical facility are available or unavailable at specific time periods (including past, present and/or future time periods).

In an example embodiment (as depicted in FIG. 1), a system 10 for predicting availability of medical facility beds is provided. Such a system 10 may be linked to and/or be in communication with medical facility patient database(s) 16. Medical facility patient database(s) 16 may include a centralized patient record system storing patient information for the medical facility. In some embodiments, the system 10 may have read access to the medical facility patient database(s) 16, but may not be able to modify the information. In some embodiments, the system 10 may copy at least a portion of the patient information from the medical facility patient database(s) 16 to generate a local patient database within the system 10. The system 10 may include medical facility bed database(s) 18, a medical facility patient stay component 20, a medical facility bed availability component 22 and a medical facility bed reporting component 24. The medical facility patient database 16 may store and/or link patient data related to a medical facility patient's biographical information, medical information and/or location information. The medical facility bed database 18 may store and/or link medical facility bed data related to location information and/or availability information. The medical facility patient stay component 20 may receive predicted length of stay data for the medical facility patients. The medical facility bed availability component 22 may reserve medical facility beds for the medical facility patient(s). Reserving may be based, at least in part, on the predicted length of stay data for the respective medical facility patient. The medical facility bed reporting component 24 may output medical facility bed availability information in a table and/or matrix configuration. Outputting may be based, at least in part, on the reservations of the medical facility bed availability component. The table configuration may include rows and columns. Each of the rows may represent a medical facility bed and each of the columns may represent a date. Medical practitioners (or their agents, employees and the like) 12 may interact with the system 10 through a communication network 26 such as the Internet, an Intranet or other similar network.

In some embodiments, the medical facility reporting component 24 may generate a graphical representation of the medical facility bed availability information. The graphical representation may be transmitted to a display device (such as a computer monitor, television or other display device) and/or a printing device (such as a computer printer or other printing device). In some embodiments, the medical facility bed reporting component 24 may display a visual representation of the availability of the medical facility beds during a past time period, a present time period and/or a future time period. Such time period may be predetermined or may be defined by a medical practitioner 12. Additionally, the medical facility reporting component 24 may generate a report depicting the medical facility bed availability information.

Medical facility bed availability information may include information related to availability, unavailability, reservations, status and the like of medical facility beds. In some embodiments, the medical facility bed availability information may include attributes relating to the predicted length of stay data. In an example embodiment, attributes relating to the predicted length of stay data may include an attribute that indicates that predicted length of stay data has been received and/or entered, an attribute that indicates that predicted length of stay data has not been received and/or entered, an attribute that indicates that the end of the predicted length of stay is approaching, an attribute that indicates that an end of the predicted length of stay has occurred, and an attribute that indicates that a medical facility patient has been discharged prior to the end of the predicted length of stay. These attributes are merely examples of attributes that may be present in various embodiments.

In some embodiments, the attributes may be depicted by a different color (or shade thereof). Some embodiments may provide for an attribute to be depicted by a red color, an attribute to be depicted by a green color and an attribute to be depicted by a yellow color. In an example embodiment, an attribute that indicates that predicted length of stay data has been received and/or entered may be depicted by a first color (light green, for example), an attribute that indicates that predicted length of stay data has not been received and/or entered may be depicted by a second color (royal blue, for example), an attribute that indicates that the end of the predicted length of stay is approaching may be depicted by a third color (yellow, for example), an attribute that indicates that an end of the predicted length of stay has occurred may be depicted by a fourth color (red, for example), and an attribute that indicates that a medical facility patient has been discharged prior to the end of the predicted length of stay may be depicted by a fifth color (dark green, for example).

In some embodiments, a medical practitioner may provide predicted length of stay data for medical facility patients. The predicted length of stay may be determined by the medical practitioner after diagnosis of a respective medical facility patient. Such predicted length of stay may be based on any number of factors determined by the medical practitioner. These may include subjective factors (such as a particular medical practitioner's knowledge based on his/her experiences and/or education, for example) and/or objective factors (such as mandatory and/or suggested treatments, for example). In some embodiments, the medical information stored in the medical facility patient database(s) may include treatment information related to a disease, an ailment, a diagnosis, a symptom, a complaint, an administered treatment and/or a proposed treatment.

Figure 2:
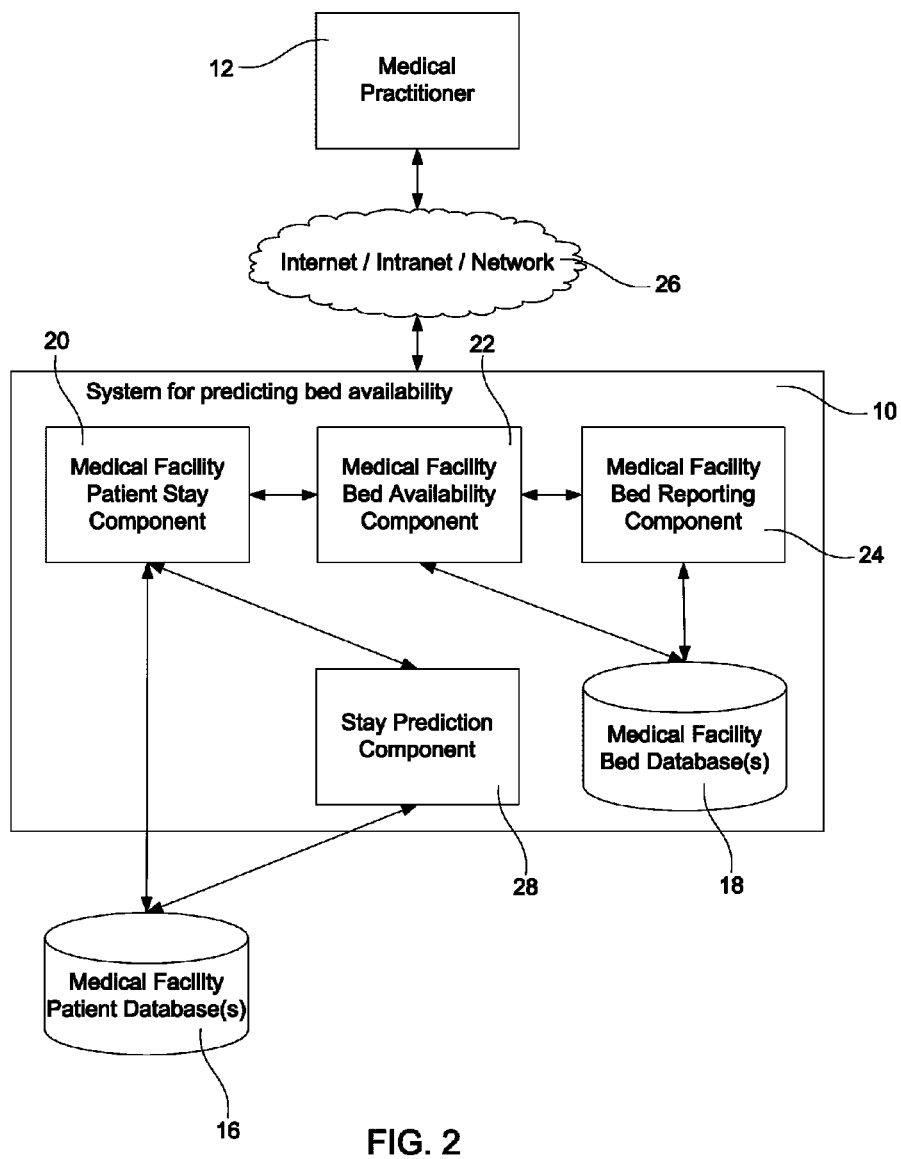
FIG. 2 is a diagram depicting another example embodiment of the present invention.

In another example embodiment (as depicted in FIG. 2), a system 10 for predicting availability of medical facility beds is provided. Such a system 10 may be linked to and/or be in communication with medical facility patient database(s) 16. Medical facility patient database(s) 16 may include a centralized patient record system storing patient information for the medical facility. The system 10 may include medical facility bed database(s) 18, a medical facility patient stay component 20, a medical facility bed availability component 22 and a medical facility bed reporting component 24, as provided in FIG. 1. This system 10 may also include a stay prediction component 28. The stay prediction component 28 may estimate the predicted length of stay data. Estimating may be based, at least in part, on historical length of stay data for the medical facility patient(s).

Figure 3:
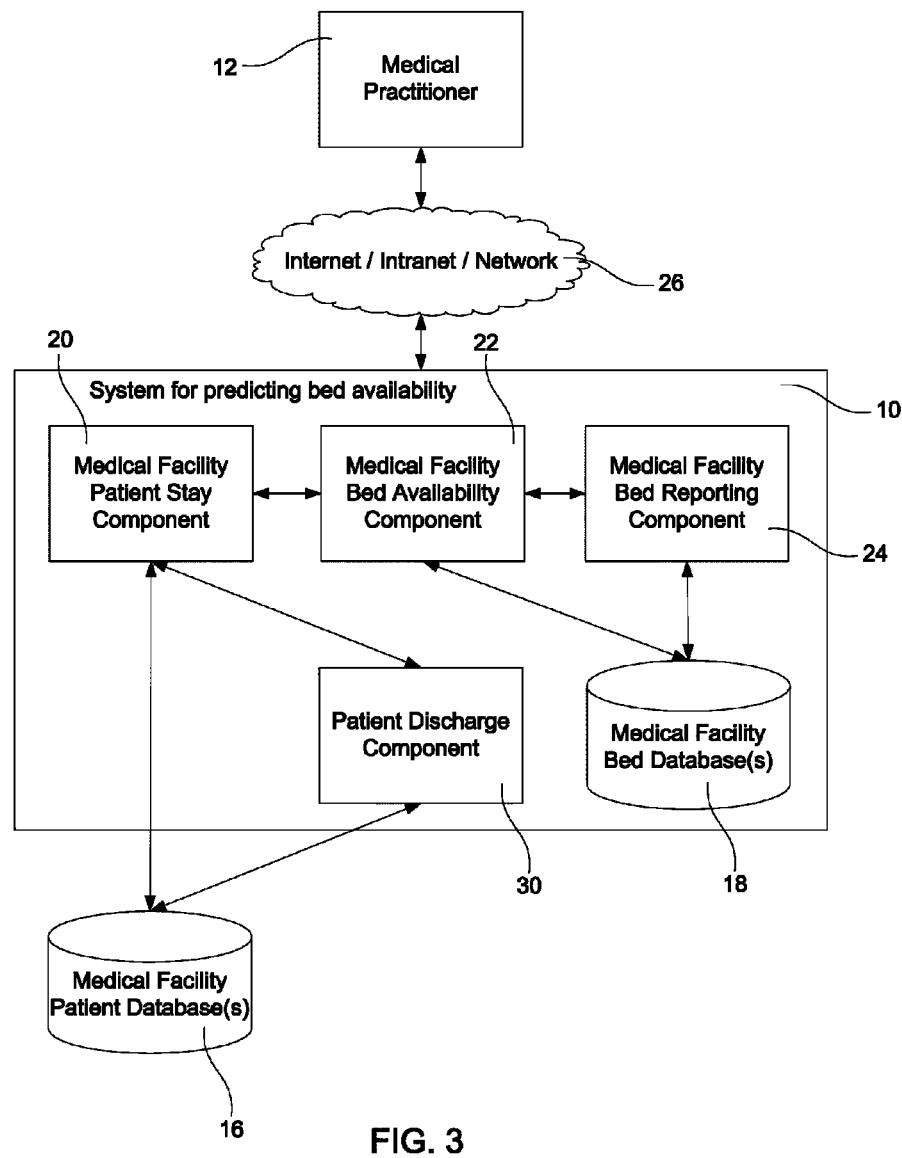
FIG. 3 is a diagram depicting yet another example embodiment of the present invention.

In yet another example embodiment (as depicted in FIG. 3), a system 10 for predicting availability of medical facility beds is provided. Such a system 10 may be linked to and/or be in communication with medical facility patient database(s) 16. Medical facility patient database(s) 16 may include a centralized patient record system storing patient information for the medical facility. The system 10 may include medical facility bed database(s) 18, a medical facility patient stay component 20, a medical facility bed availability component 22 and a medical facility bed reporting component 24, as provided in FIG. 1. This system 10 may also include a patient discharge component 30. The patient discharge component 30 may generate a list of discharge tasks to be completed by medical practitioner(s) (or their agents, employees and the like) 12 prior to discharging the medical facility patient(s).

Figure 4:
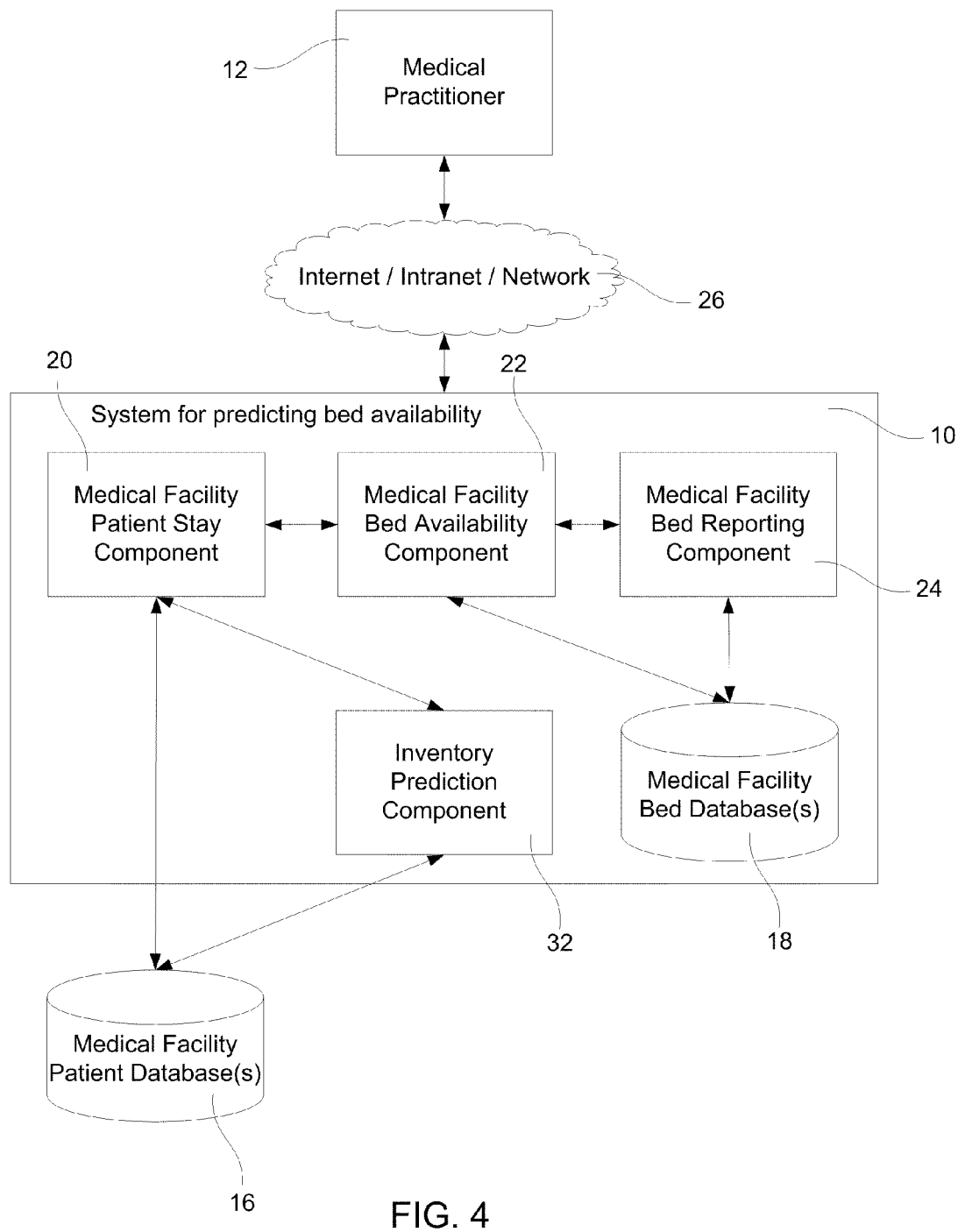
FIG. 4 is a diagram depicting even another example embodiment of the present invention.

In another example embodiment (as depicted in FIG. 4), a system 10 for predicting availability of medical facility beds is provided. Such a system 10 be linked to and/or be in communication with include medical facility patient database(s) 16. Medical facility patient database(s) 16 may include a centralized patient record system storing patient information for the medical facility. The system 10 may include medical facility bed database(s) 18, a medical facility patient stay component 20, a medical facility bed availability component 22 and a medical facility bed reporting component 24, as provided in FIG. 1. This system 10 may also include an inventory prediction component 32. The inventory prediction component 32 may monitor stocked medical supplies related to a treatment of medical facility patients. The inventory prediction component 32 may also estimate an amount of predicted medical supplies needed to perform the treatment of each of the medical facility patients. In some embodiments, the inventory prediction component 32 may generate a report depicting the amount of stocked medical supplies and/or the amount of predicted medical supplies. The inventory prediction component 32 may also interface and/or communicate internally with those responsible for ordering and/or stocking supplies or externally with third party medical supply suppliers to order additional medical supplies.

Figure 5:
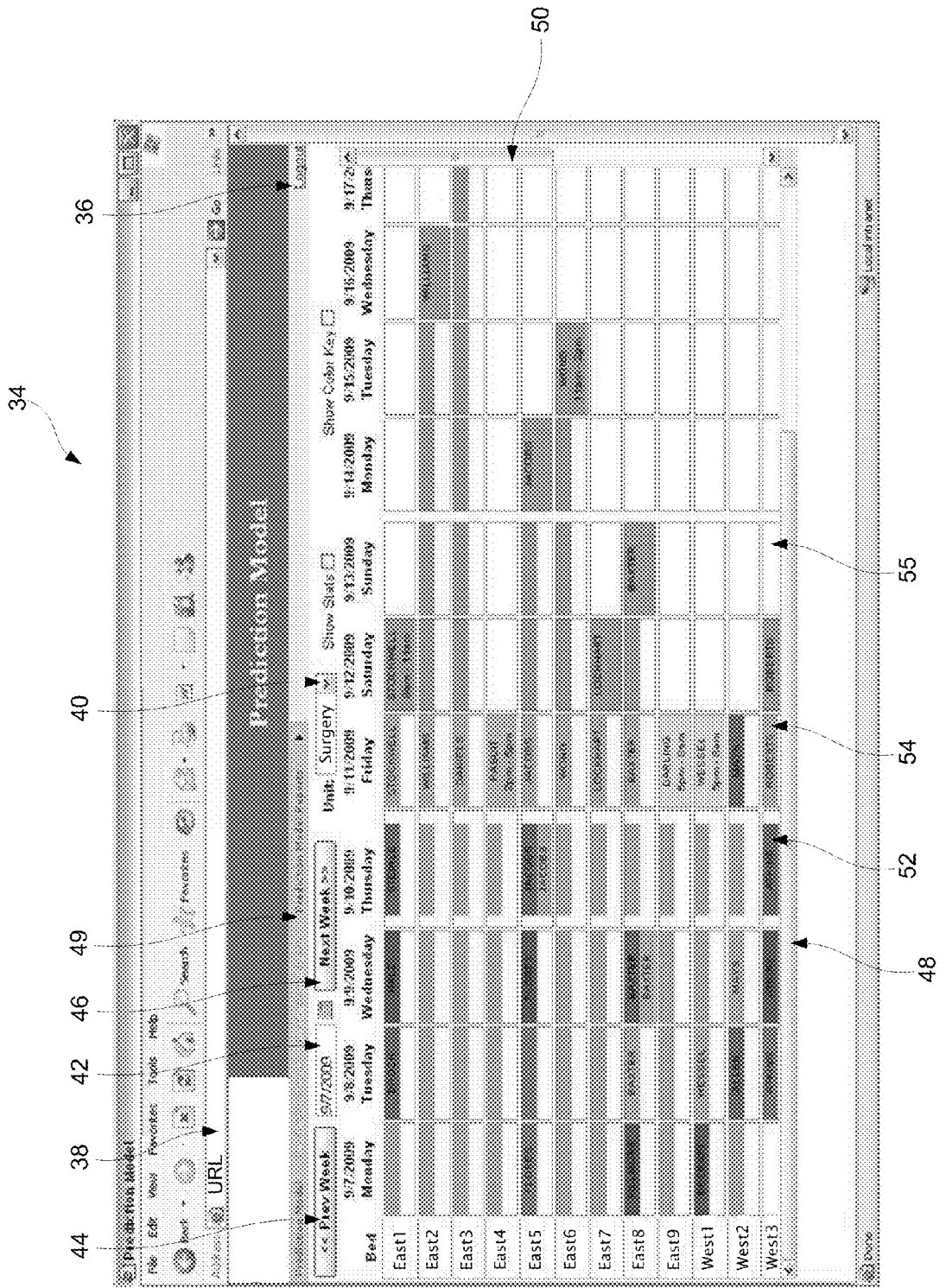
FIG. 5 is a diagram depicting an interface of an example embodiment of the present invention.

In another example embodiment (as depicted in FIG. 5), an interface 34 of a system 10 for predicting availability of medical facility beds is provided. The interface 34 depict an "at a glance" representation of the availability (or unavailability) of medical facility beds during a time period (past, present and/or future). Such an interface 34 may allow a medical practitioner to view which patients occupied which beds during a given time in the previous day, week, month and/or year. Also, the interface 34 may allow a medical practitioner to view which patients currently occupy which beds. Further, the interface 34 may allow a medical practitioner to view which patients are scheduled, reserved and/or are expected to occupy which beds in upcoming days, weeks, months and/or years.

As depicted in FIG. 5, the interface 34 may provide for access by users who are authorized to view such information. Medical facility administrators may desire that only certain people may view this information. For example, doctors and nurses may be given access to the interface 34 by way of a general or unique username and/or password. Food services employees, for example, may not be given access to the interface 34. The interface may include a link and/or button to log in and log out 36 system 10 users.

Medical practitioners having an authentic username and/or password may initiate the interface 34 by inputting a Uniform Resource Locator (URL) 38 or otherwise executing a link to the interface 34. The medical practitioner may be associated with one or more department or unit within a medical facility. For example, the medical practitioner may be a physician who primarily works in a Surgery unit. If the medical practitioner is affiliated with and/or works in multiple units, the interface 34 may provide for viewing the each of that medical practitioner's affiliated units by way of a unit selector 40.

In an example embodiment, the interface 34 may include a table having rows and columns, where the rows may represent a bed and the columns may represent a date. The table may display an indication of the actual occupancy status of a bed (for a past and/or present time period) and/or the predicted occupancy status of a bed (for a future time period). In this manner, medical practitioners may view a visual indication of the occupancy status of one or more beds in a medical facility. In some embodiments, the rows may represent a date and the columns may represent a bed.

The interface 34 may also provide various controls related to the time period to be displayed. A date selector 42 may allow a medical practitioner to locate and display bed availability on a specific date (in the past, present and/or future). The date selector 42 may include a drop down box selector, a pop-up calendar selector and/or other similar input mechanism. Additionally, medical practitioners may change the displayed time period on a weekly basis using a "previous week" link 44 and/or a "next week" link 46. Further, medical practitioners may change the displayed time period on a daily basis by manipulating the timeline selector 48.

Medical practitioners may also change which beds are to be displayed. By manipulating the bed display selector 50, medical practitioners may scroll through a list of beds in their unit until they discover the bed(s) that you desire to be displayed.

In an example embodiment, the interface 34 may provide a timeline based matrix displaying a list of beds (in a medical facility or a unit thereof) on a daily basis. As shown in FIG. 5, entry 52 displays that patient "Atkins" occupied bed "West3" on Sep. 10, 2009. Entry 54 displays that patient "Roberts" occupied bed "West3" on the following day, Sep. 11, 2009. This example displays that Roberts is scheduled to continue occupying West3 through Sep. 12, 2009. Assuming that the current date is Sep. 11, 2009, the example of FIG. 5 identifies past bed occupants, current bed occupants and future (predicted) bed occupants. FIG. 5 also displays "blank" areas for some beds, such as that depicted for bed West3 on Sep. 13, 2009. In some embodiments, a blank area 55 may represent that a bed (West3, in the example shown in FIG. 5) is not scheduled to be occupied. Should West3 be reserved for a patient scheduled to arrive on Sep. 13, 2009, the blank area 55 may be replaced by the name of the incoming patient.

In some embodiments, the medical practitioner may desire to retrieve additional information about a patient who previously occupied a bed, a patient currently occupying a bed and/or a patient scheduled to occupy a bed in the future. Such information may be viewed upon navigating a cursor directed by an input device (such as a computer mouse or a finger, for example) over an area representing a bed. By placing the input device over a bed area, a pop-up display may be viewed. The pop-up display may include information related to the bed and/or the patient. Example information may include patient room/bed numbers, patient names, patient medical record numbers, patient service teams, patient diagnosis, predicted patient discharge time and/or predicted patient discharge date, among other items. In an example embodiment, by positioning the cursor over an area and actuating the input device (such as clicking a computer mouse or tapping a touch screen device, for example), a discharge information display 56 may be viewed, as described below.

Figure 6:
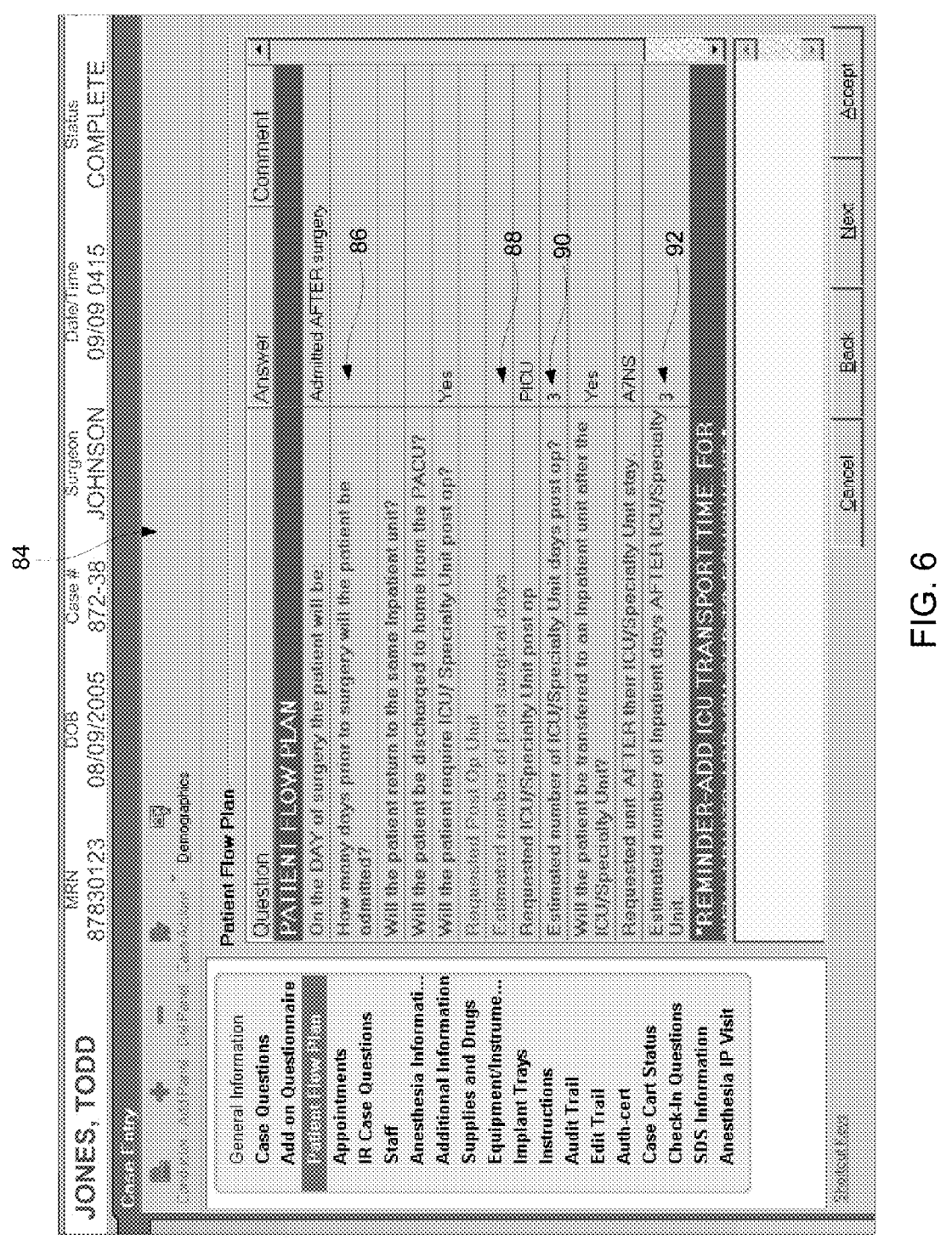

In an example embodiment, the patient information that is displayed by the interface 34 may originate from a medical practitioner. As depicted in FIG. 6, a medical practitioner may receive input patient information during a patient intake and/or admittance process using an intake interface 84. At such time, the medical practitioner may also make a determination as to a diagnosis, treatment and/or other related procedure. Further, the medical practitioner may make a determination as to how long the patient is projected to be admitted at the medical facility. Such a determination may also include a determination of how long a patient may be admitted to various divisions within the medical facility. For example, the intake interface 84 may provide areas 86, 88, 90, 92 where medical practitioners may input estimated days a patient may be admitted (thus requiring a bed) prior to surgery, estimated days a patient may remain admitted after a surgery, estimated days of post-surgery special and/or intensive care, and/or estimated days of inpatient days after leaving a special and/or intensive care unit. In FIG. 6, patient "Todd Jones" is estimated (by a medical practitioner performing a patient intake process) to spend three days in an intensive care unit after surgery and three days in an inpatient unit after leaving the intensive care unit.

Figure 7:
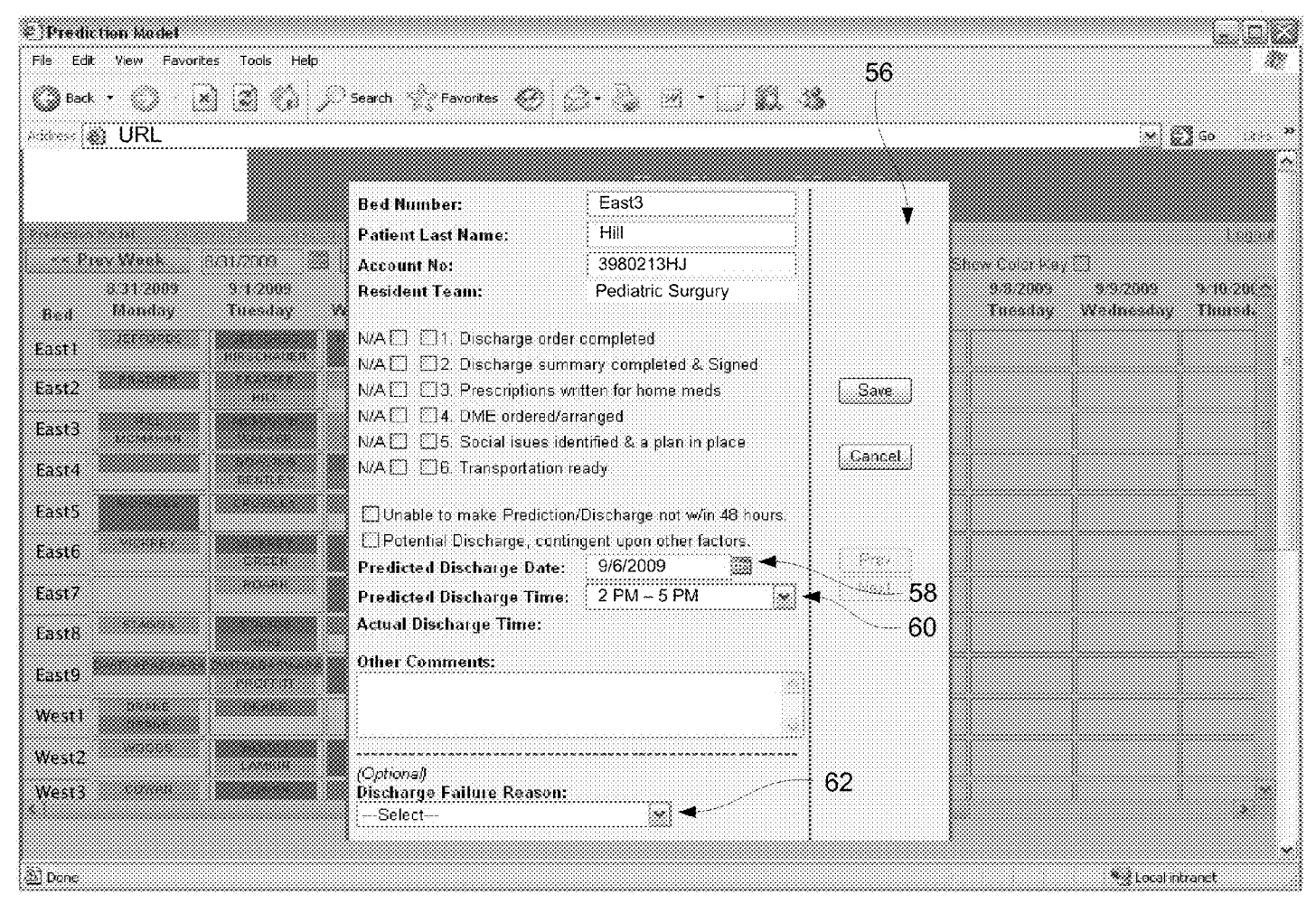

In another example embodiment (as depicted in FIG. 7), an interface 34 of a system 10 for predicting availability of medical facility beds is provided. A discharge information display 56 may be viewed by the medical practitioner to view information related to a patient's discharge from the medical facility (or at least the unit they are currently occupying). Such information may be viewed, entered and/or edited using the predicted discharge date selector 58 and/or the predicted discharge time selector 60. The medical practitioner may also input comments related to the patient's discharge. Using the discharge failure reason selector 62, the medical practitioner may also identify reasons (if any) for the patient's failing to be discharged by the predicted discharge date/time.

The system 10 may generate reports to assist medical practitioners in viewing, analyzing, tracking and/or revising a patient's discharge (actual and/or predicted) information. The system 10 may generate reports using the interface's 34 prediction model reports selector 49. A medical practitioner may then choose the type of report to generate.

FIG. 8 depicts an example report that may be generated by an example embodiment of the present invention. The daily discharge prediction worksheet 64 may be displayed and/or printed for use by medical practitioners. Example information on the discharge prediction worksheet 64 may include patient room/bed numbers, patient names, patient medical record numbers, patient service teams, a patient's potential for discharge, a checklist of tasks that may be completed prior to patient discharge, patient predicted discharge time and/or patient predicted discharge date, among other items.

Figure 9:
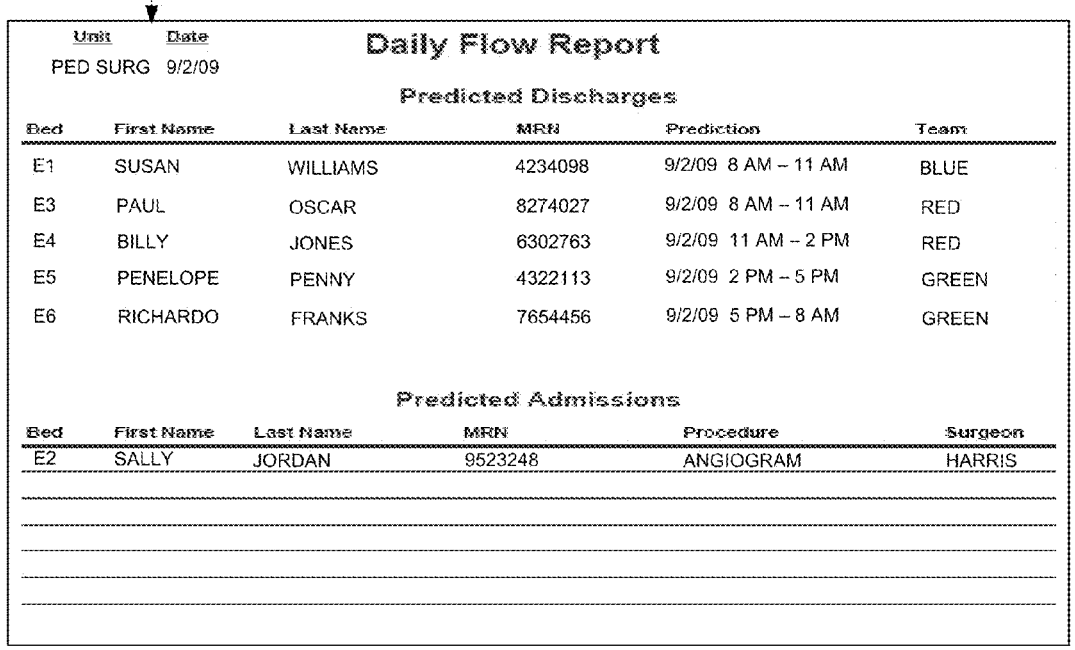
FIG. 9 depicts an example report that may be generated by another example embodiment of the present invention.

FIG. 9 depicts an example report that may be generated by another example embodiment of the present invention. The daily flow report 66 may be displayed and/or printed for use by medical practitioners. An example daily flow report 66 may display information regarding a specific date's predicted patient discharges and predicted admissions. Example information on the daily flow report 66 may include patient room/bed numbers, patient names, patient medical record numbers, patient service teams, patient predicted discharge time, patient predicted discharge date, predicted admittee names, predicted admittee medical record numbers, predicted admittee procedures and/or medical practitioners associated with the predicted admittee, among other items.

Figure 10:
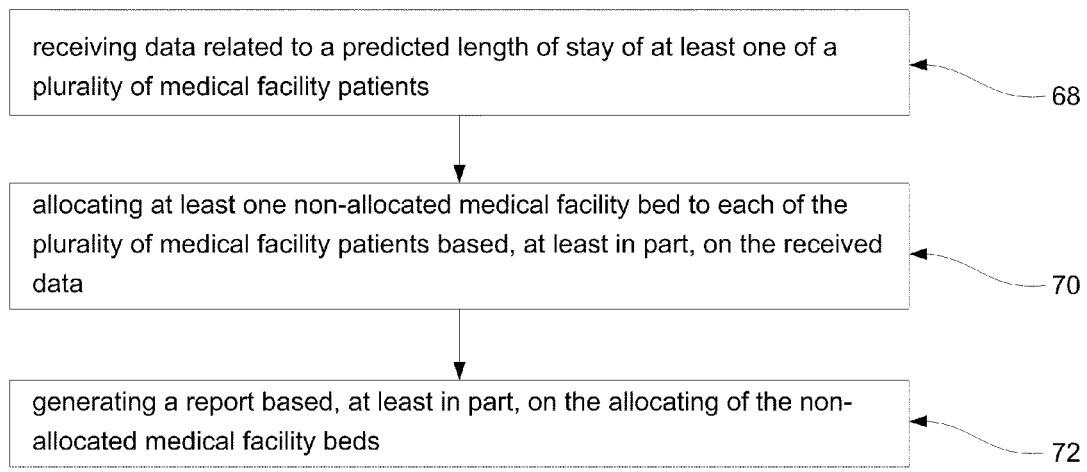
FIG. 10 is a flow diagram depicting an example embodiment of the present invention.

As depicted in FIG. 10, a method of predicting availability of medical facility beds is provided. Such a method may include processing operations 68, 70 and/or 72. Beginning at operation 68, data related to a predicted length of stay of medical facility patient(s) may be received. Operation 70 may include allocating non-allocated medical facility bed(s) to the medical facility patient(s). This allocation (operation 70) may be based, at least in part, on the data received (from operation 68). Continuing from operation 70, operation 72 may include generating a report, which may be based, at least in part, on the allocating (from operation 70) of the non-allocated medical facility beds. The report may include a table having rows and columns. Each row may be representative of a medical facility bed and each column may be representative of a date. In some examples, the method may be implemented as a web server, a computer-readable medium having instructions thereon and/or a memory device having software operating thereon.

Figure 11:
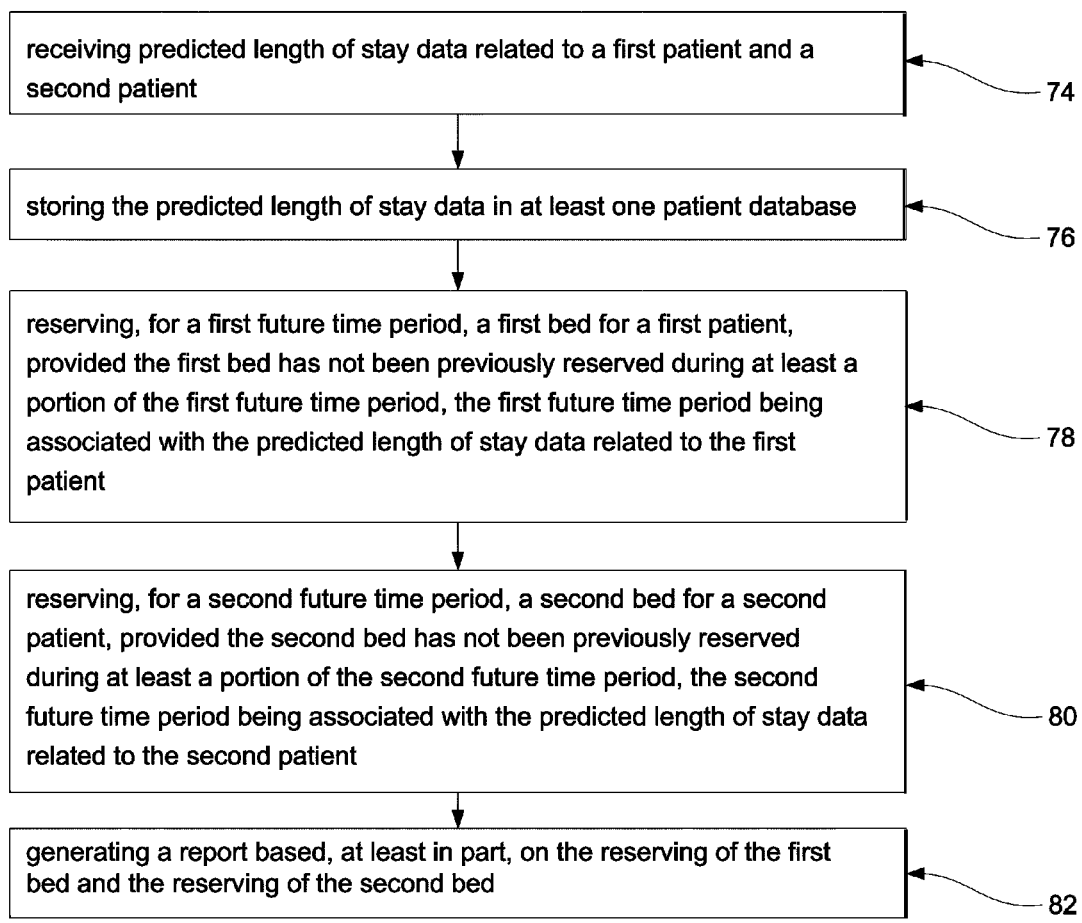
FIG. 11 is a flow diagram depicting yet another example embodiment of the present invention.

As depicted in FIG. 11, a method of allocating beds in a medical facility among patients is provided. Such a method may include processing operations 74, 76, 78, 80 and/or 82. Beginning at operation 74, predicted length of stay data related to a first patient and a second patient may be received. Operation 76 may include storing the predicted length of stay data in patient database(s). Continuing from operation 76, operation 78 may include reserving (for a first future time period) a first bed for a first patient. This reserving (operation 78) may reserve the first bed if the first bed has not been previously reserved during a portion (or the entirety) of the first future time period. The first future time period may correlate with the predicted length of stay data related to the first patient. Operation 80 may include reserving (for a second future time period) a second bed for a second patient. This reserving (operation 80) may reserve the second bed if the second bed has not been previously reserved during a portion (or the entirety) of the second future time period. The second future time period may correlate with the predicted length of stay data related to the second patient. Operation 82 continues with generating a report based, at least in part, on the reserving of the first bed and the reserving of the second bed. The report may include a table having rows and columns. One row may be representative of the first bed and another row may be representative of the second bed. Each column may be representative of a date. In some embodiments, a visual representation of the first bed, the second bed and/or reservation status of the first bed and second bed may be generated and displayed on a display device for viewing by a medical practitioner. In some examples, the method may be implemented as a web server, a computer-readable medium having instructions thereon and/or a memory device having software operating thereon.

Medical practitioners may utilize the method depicted in FIG. 11 to view a visual representation of the which beds are scheduled as occupied at past, present and/or future times. Such a method may allow the medical practitioner to view and/or select (or reserve) open or unreserved beds for future time periods. In this manner, a medical practitioner may easily determine the occupancy status of each bed in a medical facility (or department thereof).

In some embodiments, the predicted length of stay may be generated by an artificial intelligence component. Such a component may be instructed to predict and/or estimate patient length of stay information based on data. As will be understood by those of ordinary skill, the artificial intelligence component prediction may be based upon a knowledge base that associates historical patient stay terms with other historical factors such as, without limitation, patient medical history, patient insurance data, historical disease/ailment data, historical treatment data, historical length of stay data, historical recovery time data, and the like. In some embodiments, the artificial intelligence component may be as accurate as medical practitioner or more accurate than medical practitioner at predicting a patient's length of stay.

In some embodiments, a method of assessing a medical supply inventory is provided. Such methods may include receiving a current inventory value for a medical product, receiving patient information related to bed occupancy, diagnosis, disease/ailment, and/or treatment, generating a predicted inventory value for the medical product based, at least in part, on the patient information, and generating an inventory report including the current inventory value, the patient information and/or the predicted inventory value. The inventory report may assist medical practitioners and/or medical facility administrator in ordering an appropriate amount of the medical product to have enough of the medical product on hand for patient needs.

To provide additional context for various aspects of the present invention, the following discussion is intended to provide a brief, general description of a suitable computing environment in which the various aspects of the invention may be implemented. While one embodiment of the invention relates to the general context of computer-executable instructions that may run on one or more computers, those skilled in the art will recognize that the invention also may be implemented in combination with other program modules and/or as a combination of hardware and software.

Generally, program modules include routines, programs, components, data structures, etc., that perform particular tasks or implement particular abstract data types. Moreover, those skilled in the art will appreciate that aspects of the inventive methods may be practiced with other computer system configurations, including single-processor or multi-processor computer systems, minicomputers, mainframe computers, as well as personal computers, hand-held wireless computing devices, microprocessor-based or programmable consumer electronics, and the like, each of which can be operatively coupled to one or more associated devices. Aspects of the invention may also be practiced in distributed computing environments where certain tasks are performed by remote processing devices that are linked through a communications network. In a distributed computing environment, program modules may be located in both local and remote memory storage devices.

A computer may include a variety of computer readable media. Computer readable media may be any available media that can be accessed by the computer and includes both volatile and nonvolatile media, removable and non-removable media. By way of example, and not limitation, computer readable media may comprise computer storage media and communication media. Non-transitory computer storage media includes volatile and nonvolatile, removable and non-removable media implemented in any method or technology for storage of information such as computer readable instructions, data structures, program modules or other data. Non-transitory computer storage media includes, but is not limited to, RAM, ROM, EEPROM, flash memory or other memory technology, CD ROM, digital video disk (DVD) or other optical disk storage, magnetic cassettes, magnetic tape, magnetic disk storage or other magnetic storage devices, or any other medium which may be used to store the desired information and which may be accessed by the computer.

An exemplary environment for implementing various aspects of the invention may include a computer that includes a processing unit, a system memory and a system bus. The system bus couples system components including, but not limited to, the system memory to the processing unit. The processing unit may be any of various commercially available processors. Dual microprocessors and other multi processor architectures may also be employed as the processing unit.

The system bus may be any of several types of bus structure that may further interconnect to a memory bus (with or without a memory controller), a peripheral bus, and a local bus using any of a variety of commercially available bus architectures. The system memory may include read only memory (ROM) and/or random access memory (RAM). A basic input/output system (BIOS) is stored in a non-volatile memory such as ROM, EPROM, EEPROM, which BIOS contains the basic routines that help to transfer information between elements within the computer, such as during start-up. The RAM may also include a high-speed RAM such as static RAM for caching data.

The computer may further include an internal hard disk drive (HDD) (e.g., EIDE, SATA), which internal hard disk drive may also be configured for external use in a suitable chassis, a magnetic floppy disk drive (FDD), (e.g., to read from or write to a removable diskette) and an optical disk drive, (e.g., reading a CD-ROM disk or, to read from or write to other high capacity optical media such as the DVD). The hard disk drive, magnetic disk drive and optical disk drive may be connected to the system bus by a hard disk drive interface, a magnetic disk drive interface and an optical drive interface, respectively. The interface for external drive implementations includes at least one or both of Universal Serial Bus (USB) and IEEE 1394 interface technologies.

The drives and their associated computer-readable media may provide nonvolatile storage of data, data structures, computer-executable instructions, and so forth. For the computer, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules may be stored in the drives and RAM, including an operating system, one or more application programs, other program modules and program data. All or portions of the operating system, applications, modules, and/or data may also be cached in the RAM. It is appreciated that the invention may be implemented with various commercially available operating systems or combinations of operating systems.

It is within the scope of the disclosure that a user may enter commands and information into the computer through one or more wired/wireless input devices, for example, a touch screen display, a keyboard and/or a pointing device, such as a mouse. Other input devices may include a microphone (functioning in association with appropriate language processing/recognition software as know to those of ordinary skill in the technology), an IR remote control, a joystick, a game pad, a stylus pen, or the like. These and other input devices are often connected to the processing unit through an input device interface that is coupled to the system bus, but may be connected by other interfaces, such as a parallel port, an IEEE 1394 serial port, a game port, a USB port, an IR interface, etc.

A display monitor or other type of display device may also be connected to the system bus via an interface, such as a video adapter. In addition to the monitor, a computer may include other peripheral output devices, such as speakers, printers, etc.

The computer may operate in a networked environment using logical connections via wired and/or wireless communications to one or more remote computers. The remote computer(s) may be a workstation, a server computer, a router, a personal computer, a portable computer, a personal digital assistant, a cellular device, a microprocessor-based entertainment appliance, a peer device or other common network node, and may include many or all of the elements described relative to the computer. The logical connections depicted include wired/wireless connectivity to a local area network (LAN) and/or larger networks, for example, a wide area network (WAN). Such LAN and WAN networking environments are commonplace in offices, and companies, and facilitate enterprise-wide computer networks, such as intranets, all of which may connect to a global communications network such as the Internet.

The computer may be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi (such as IEEE 802.11x (a, b, g, n, etc.)) and Bluetooth™ wireless technologies. Thus, the communication may be a predefined structure as with a conventional network or simply an ad hoc communication between at least two devices.

The system may also include one or more server(s). The server(s) may also be hardware and/or software (e.g., threads, processes, computing devices). The servers may house threads to perform transformations by employing aspects of the invention, for example. One possible communication between a client and a server may be in the form of a data packet adapted to be transmitted between two or more computer processes. The data packet may include a cookie and/or associated contextual information, for example. The system may include a communication framework (e.g., a global communication network such as the Internet) that may be employed to facilitate communications between the client(s) and the server(s).

For the purpose of this disclosure, a "component" may be any computer hardware, software or other related instrumentalities (or a combination of such or any multiple of such) configured to perform as described and claimed herein. It should also be understood that two or more individual "components" can be sharing or combined with computer hardware, software and other related instrumentalities of each other. For example, and without limitation, a single computer server or even a computer cloud may comprise two or more recited components.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. One or more non-transitory computer memory devices including computer readable instructions for controlling a computerized system to perform a method of predicting availability of a plurality of medical facility beds, the instructions comprising the steps of:
generating a predicted length of stay data related to a first patient and a second patient based on a knowledge base that associates historical patient stay data related to the first patient and the second patient with other historical data;
receiving the predicted length of stay data related to the first patient and the second patient;
storing the predicted length of stay data in at least one patient database;
reserving, for a first future time period, a first bed for a first patient, provided the first bed has not been previously reserved during at least a portion of the first future time period, the first future time period being associated with the predicted length of stay data related to the first patient;
reserving, for a second future time period, a second bed for a second patient, provided the second bed has not been previously reserved during at least a portion of the second future time period, the second future time period being associated with the predicted length of stay data related to the second patient;
generating a report based, at least in part, on the reserving of the first bed and the reserving of the second bed, the report comprising a table having at least two rows and a plurality of columns, each of the plurality of columns representing a respective date, wherein a first row of the at least two rows represents the first bed and a second row of the at least two rows represents the second bed, the table representing an availability information of each of the first bed and the second bed; and,
wherein the other historical data comprises patient medical history, patient insurance data, historical disease/ailment data, historical treatment data, historical length of stay data and historical recovery time data.

2. The one or more non-transitory computer memory devices of claim 1, including computer readable instructions for controlling a computerized system, further comprising:
displaying a visual representation of the availability of at least the first bed and the second bed during at least one of a past time period, a present time period and a future time period.

3. The one or more non-transitory computer memory devices of claim 1, including computer readable instructions for controlling a computerized system, wherein
an input component is configured to receive the predicted length of stay data from at least one medical practitioner.

4. The one or more non-transitory computer memory devices of claim 3, including computer readable instructions for controlling a computerized system, wherein
the predicted length of stay data for the first patient and the second patient may be determined by a medical practitioner after a diagnosis of the respective medical facility patient; and
wherein the diagnosis is based on at least one of subjective factors, and at least one of objective factors.

5. The one or more non-transitory computer memory devices of claim 3, including computer readable instructions for controlling a computerized system, wherein the input component is configured to receive diagnosis data.

6. The one or more non-transitory computer memory devices of claim 1, including computer readable instructions for controlling a computerized system, further comprising:
generating a list of discharge tasks to be completed by at least one medical practitioner prior to discharging the first patient or the second patient.

7. The one or more non-transitory computer memory devices of claim 1, including computer readable instructions for controlling a computerized system, wherein:
an artificial intelligence component is configured to generate the predicted length of stay data based.

8. The one or more non-transitory memory devices of claim 1, including computer readable instructions for controlling a computerized system, wherein the memory devices are located on one more Web servers.

9. The one or more non-transitory computer memory devices of claim 1, including computer readable instructions for controlling a computerized system, wherein:
the patient database is configured to store patient data related to at least one of biographical information, medical information and location information of the first patient or the second patient.

10. The one or more non-transitory computer memory devices of claim 9, including computer readable instructions for controlling a computerized system, wherein the medical information comprises treatment information related to at least one of a disease, an ailment, a diagnosis, a symptom, a complaint, an administered treatment and a proposed treatment.

11. The one or more non-transitory computer memory devices of claim 1, including computer readable instructions for controlling a computerized system, further comprising:
storing in at least one medical facility bed database, data related to at least one of location information, reservation information, and availability information for at least the first bed and the second bed.

12. The one or more non-transitory computer memory devices of claim 1, including computer readable instructions for controlling a computerized system, wherein:
the report is transmitted to at least one of a display device and a printing device.

13. The one or more non-transitory computer memory devices of claim 1, including computer readable instructions for controlling a computerized system, wherein the predicted length of stay data comprises a plurality of attributes relating to the medical facility bed availability information.

14. The one or more non-transitory computer memory devices of claim 13, including computer readable instructions for controlling a computerized system, wherein each of the plurality of attributes is represented by a respective color.

15. The one or more non-transitory computer memory devices of claim 13, including computer readable instructions for controlling a computerized system, wherein the plurality of attributes comprise at least one of a predicted length of stay data is present attribute, a predicted length of stay data is not present attribute, an end of the predicted length of stay is approaching attribute, an end of the predicted length of stay has occurred attribute, and a medical facility patient has been discharged prior to the end of the predicted length of stay attribute.

16. The one or more non-transitory computer memory devices of claim 15, including computer readable instructions for controlling a computerized system, wherein the predicted length of stay data is present attribute is represented by a first color, the predicted length of stay data is not present attribute is represented by a second color, an end of the predicted length of stay is approaching attribute is represented by a third color, an end of the predicted length of stay has occurred attribute is represented by a fourth color, and the medical facility patient has been discharged prior to the end of the predicted length of stay attribute is represented by a fifth color.

* * * * *